US008920386B2

(12) United States Patent
Cefai et al.

(10) Patent No.: US 8,920,386 B2
(45) Date of Patent: *Dec. 30, 2014

(54) MICRO-VALVE

(75) Inventors: Joseph John Cefai, Treboeth (GB); Julian Llewellyn Shapley, Cardiff (GB)

(73) Assignee: Cellnovo, Ltd., Swansea (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/278,426

(22) Filed: Oct. 21, 2011

(65) Prior Publication Data

US 2012/0130311 A1    May 24, 2012

Related U.S. Application Data

(63) Continuation of application No. 12/447,223, filed as application No. PCT/GB2007/004071 on Oct. 25, 2007, now Pat. No. 8,048,041.

(30) Foreign Application Priority Data

Oct. 26, 2006 (GB) .................................. 0621343.3

(51) Int. Cl.
A61M 5/00 (2006.01)
A61M 5/315 (2006.01)
A61M 37/00 (2006.01)
A61M 1/00 (2006.01)
A61M 39/24 (2006.01)
F16K 99/00 (2006.01)

(52) U.S. Cl.
CPC ............ A61M 39/24 (2013.01); F16K 99/0001 (2013.01); F16K 99/0015 (2013.01); A61M 2039/2433 (2013.01); A61M 2039/246 (2013.01); A61M 2205/0244 (2013.01); A61M 2205/0294 (2013.01); F16K 2099/0086 (2013.01); F16K 2099/0094 (2013.01)

USPC ........... 604/247; 604/246; 604/236; 604/131; 604/151

(58) Field of Classification Search
CPC ............... A61M 2039/2433; A61M 2039/246; A61M 2205/0294; A61M 2205/0272; A61M 39/24; A61M 39/22; F16K 2099/0086; F16K 2099/0082; F16K 99/0001; F16K 99/0015; F16K 99/0003
USPC .......... 604/236, 131, 30, 890.1, 246, 247, 34, 604/151, 167.03; 137/511; 417/437
See application file for complete search history.

(56) References Cited

U.S. PATENT DOCUMENTS

| 4,152,098 | A | * | 5/1979 | Moody et al. | .............. 417/413.1 |
| 4,858,619 | A | * | 8/1989 | Toth | .............................. 600/561 |
| 7,291,133 | B1 | | 11/2007 | Kindler et al. | |
| 2005/0258581 | A1 | | 11/2005 | Tanaka | |
| 2009/0299300 | A1 | * | 12/2009 | Truitt et al. | .................... 604/246 |

* cited by examiner

FOREIGN PATENT DOCUMENTS

| DE | 19723648 C1 | 8/1998 |
| GB | 875034 | 8/1961 |
| WO | 02068823 A1 | 9/2002 |

Primary Examiner — Bhisma Mehta
Assistant Examiner — Bradley G Thomas, Jr.
(74) Attorney, Agent, or Firm — Roy P. Issac; Carolyn S. Elmore, Esq.; Elmore Patent Law Group, P.C.

(57) ABSTRACT

A one-way valve (1) comprises a seat (5) and a membrane (4) having an inner portion (4a) that is stretched over the seat, wherein, in use, the inner membrane portion is selectively deflected from the seat such that a fluid path is created from one side of the membrane to the other so as to open the valve, and wherein an outer peripheral portion (4b) of the membrane is stiffer than the inner portion such that the membrane deflection is substantially restricted to only the inner portion. The one-way valve may be used in a pump for an infusion system.

31 Claims, 4 Drawing Sheets

US 8,920,386 B2

MICRO-VALVE

RELATED APPLICATION(S)

This application is a continuation of U.S. application Ser. No. 12/447,223, filed Jan. 15, 2010, now U.S. Pat. No. 8,048,041, which is a US National stage entry of International Application No. PCT/GB2007/004071, filed Oct. 25, 2007, which international application was published on May 2, 2008 as International Publication WO 2008/050126. The International Application claims priority of British Patent Application 0621343.3, filed Oct. 26, 2006. The entire teachings of the above applications are incorporated herein by reference.

FIELD OF THE INVENTION

In devices for the programmed delivery of therapeutic products into the human or animal body, there is generally provided a pressurised reservoir of therapeutic product working in cooperation with a pumping chamber and valve means. The therapeutic product is typically pumped by the device through a tube to a cannula that pierces the patient's skin. The device can be capable of providing a variable rate of infusion of the therapeutic product to the patient over several days. This invention is directed to an improved micro-valve for the pumping chamber.

BACKGROUND TO THE INVENTION

Therapeutic products can be administered to a human or animal in a variety of ways and the administration method is often matched to the specific requirements of the therapeutic product and its intended action. While oral administration is typically preferred, some therapeutic products, such as insulin, have to be administered in such as way as to avoid the digestive system, or it may be beneficial to deliver them directly to the site of intended action.

The administration of therapeutic products to avoid the digestive tract is known as parenteral delivery and is typically achieved by administering the therapeutic product as a liquid formulation directly into the circulation. This is commonly performed using a syringe or equivalent device to deliver a bolus of therapeutic product, or an infusion system capable of continuous, and in some cases programmed, delivery of therapeutic product. It is clear that the controlled administration of the therapeutic product more adequately matches the clinical requirement of these products, often offering better therapeutic control and reducing toxicity.

There is a growing demand for intensive insulin therapies for controlling glucose in people with diabetes. These therapies require that the patient administer regular insulin in an attempt to mimic the daily pattern of insulin release in an individual without diabetes. The pattern of insulin release in people without diabetes is complex. Generally, there is a background level of insulin that acts to control a fasting glucose and this is supplemented by temporary increases that counteract glucose released from ingested meals.

To meet this demand a number of infusion systems have appeared based on positive pressure reservoirs working in cooperation with a pulsatile pumping chamber having one-way check-valves operating at the inlet and/or the outlet of the pumping chamber.

An exemplary prior art infusion system is described in U.S. Pat. No. 4,486,190. This document describes an infusion system where therapeutic product is held in a reservoir at a positive pressure. Therapeutic product is withdrawn from the reservoir through a one-way check-valve that forms an inlet valve to a pumping chamber. A flow restrictor is provided at the outlet of the pumping chamber. Drawing of a membrane of the pumping chamber increases the volume of the pumping chamber, thereby decreasing the pressure in the pumping chamber. This causes an increase in the pressure differential across the inlet valve to beyond a predetermined activation pressure of the inlet valve which opens in response. This enables the therapeutic product to enter the pumping chamber. The pumping chamber membrane moves under the action of a solenoid which, when released, causes the pumping chamber membrane to return to its original position. The inlet valve shuts under the action of a return spring and the therapeutic product empties from the pumping chamber via the outlet and the flow restrictor. The system described in U.S. Pat. No. 4,486,190 suffers a drawback in that the filling efficiency of the pumping chamber is affected by the pressure at the outlet. In addition, the design of the system is prone to allowing uncontrolled flow of therapeutic product due to leaking of the inlet valve. To prevent this, the activation pressure of the inlet valve could be increased but this would then compromise the pumping efficiency.

U.S. Pat. No. 4,152,098 describes a micro-pump for an infusion system that incorporates one-way check-valves at an inlet and an outlet of the micro-pump. Each one-way check-valve is formed by sandwiching a rubber membrane between two rigid layers. The rigid layers have a protrusion formed on one layer and a corresponding recess formed in the opposite layer at the site of the valves. A fluid conduit passes up through a center of the protrusion that is covered by the membrane. The membrane has a hole offset from an opening of the fluid conduit in the protrusion. During assembly, the membrane is located onto one of the rigid layers and held in place by gluing it to one or both of the rigid layers. The gluing of the membrane to the rigid layer(s) ensures that the membrane does not move during assembly and stretches over the protrusion to provide sealing. The need to glue the membrane during the assembly process significantly increases the complexity of the manufacture of the micro-pump. It also serves to increase the opportunity for assembly problems and seepage of the glue. These problems are significantly increased when an attempt is made to reduce the size of micro-pumps yet further.

The provision of a one-way check-valve at the outlet of the pumping chamber having a sufficiently high activation pressure to prevent free flow of liquid under expected operating conditions is necessary for micro-pumps for use in infusion systems, where uncontrolled flow of therapeutic product into the patient would be unacceptable. The activation pressure of the outlet valve can be designed to be overcome by the pressure generated by a pumping stroke of the pumping chamber. On the other hand, the one-way check-valve at the inlet could have a relatively low activation pressure, sufficient to seal but which allows the inlet valve to open readily once a filling stroke of the pumping chamber initiates.

In the above described prior art, the valves are assembled using conventional machining techniques and are relatively large. In addition, the devices described are not suitable for disposable, short term use.

WO 02/068823 describes a further passive membrane-type micro-valve formed of multiple layers having cut outs. The assembled valve includes a membrane having an aperture formed therein. A valve inlet is disposed on one side of the membrane and a valve outlet is disposed on the opposite side. A region of the membrane immediately surrounding the aperture is stretched over a valve seat on which the membrane rests when the valve is closed. Again, a positive fluid pressure in the valve inlet causes the membrane to deflect from the valve seat when above some undefined activation pressure, and fluid is then able to pass through the small aperture and from the valve outlet. A reduction in the fluid pressure permits the membrane to return to the valve seat, closing the valve. Valves of this type are slightly improved over those in U.S. Pat. No. 4,152,098 since some consideration is given to factors affecting the activation pressure. However, the membrane material is inherently flexible giving rise to misalignment of the inlet, outlet and valve seat during manufacture. This can adversely affect control of the activation pressure. It is also observed in this type of valve design that the tension of the valve membrane cannot be accurately controlled during the assembly of the device and that this leads to variability in the performance of the valve.

There is therefore a need in the art for an improved one-way micro-valve for a micro-pump, that is very small, lightweight, inexpensive and disposable, having an accurately defined activation pressure. The micro-valve should also be suitable for manufacture in a variety of sizes for various applications and having a range of accurately predetermined activation pressures. These and other objects will become apparent from the following description of the invention.

SUMMARY OF THE INVENTION

According to a first aspect of the present invention there is provided a one-way valve comprising a seat, and a membrane having an inner portion that is stretched over the seat, wherein, in use, the inner membrane portion is selectively deflected from the seat such that a fluid path is created from one side of the membrane to the other so as to open the valve, and wherein an outer peripheral portion of the membrane is stiffer than the inner portion such that the membrane deflection is substantially restricted to only the inner portion.

The present invention is advantageous in providing a one-way valve having an accurately defined activation pressure. By forming the outer portion of the membrane stiffer than the inner portion such that the membrane deflection is substantially restricted to only the inner portion, it becomes possible to align, during manufacture, the outer portion of the membrane with respect to the valve seat. Also, the deflectable portion of the membrane can be restricted to only that portion immediately adjacent the valve seat. In these ways, an accurately defined and consistent activation pressure across a batch of valves may be provided.

Stiffening of the outer membrane portion may be effected in a plurality of ways. In a preferred embodiment of the invention a rigid frame is embedded in the outer portion of the membrane. For uniform pressure distribution around the valve seat, the rigid frame may be formed as an annulus where the one-way valve is substantially symmetrical about its diameter. The rigid frame may be made of various materials, including glass, metal, ceramic and polymer.

As an alternative, or in addition, to the rigid frame embodiment, the outer portion of the membrane may have a different material composition, or dimension, to that of the inner portion. A relative stiffness of the inner and outer portions may therefore be predefined according to a desired activation pressure at which the valve opens.

In a preferred embodiment the fluid path created from one side of the membrane to the other may include a portion through at least one aperture formed in the membrane. The number and arrangement of the apertures may be selected according to a desired activation pressure at which the valve opens. It has been found that the number and arrangement of the apertures effects the operation of the valve in a number of ways.

Firstly, the apertures decrease the structural integrity of the membrane, thereby decreasing the stiffness of the membrane. Secondly, the number and arrangement of the apertures effects the volume flow rate through the valve when the valve is open. Since the volume flow rate has a significant effect on the pressure distribution across the valve, this affects the valve activation pressure as well as the valve efficiency.

The valve seat may be integrally formed with a first body portion of the one way valve. This first body portion may have a fluid conduit that defines an inlet of the valve. The inlet may be fluidically connected to the aperture(s) in the membrane, when the membrane is displaced from the valve seat as the valve opens, by a first cavity defined by a recess in the first body portion. The valve may further comprise a second body portion on the opposite side of the membrane to the first body portion, wherein the second body portion has a fluid conduit formed therethrough defining an outlet of the valve. A second cavity may be defined by a recess in the second body portion into which the inner membrane portion moves when the valve opens. The outlet may open into the second cavity such that the second cavity creates a fluid path between the aperture(s) in the membrane and the outlet. The arrangement of the cavities with respect to the inlet, outlet and aperture(s) provides efficient movement of the membrane with respect to the valve body portions whilst providing an efficient fluid path across the valve. The inlet and outlet may open directly opposite one another with respect to the membrane, or the inlet and outlet may open in a laterally offset opposing relationship with respect to the fluid flow direction through the valve.

The outer portion of the membrane may be fixed to the first body portion, or may be fixed between the first and second body portions. The fixing may be by means of clamping, clipping, gluing, bonding or welding. In this way, the relatively stiff outer portion is spatially fixed with respect to the valve body such that the inner membrane portion may be accurately spatially determined with respect to the position of the valve seat. To ensure that the outer membrane portion is fixed to the valve body correctly, a at least one of the first and second body portions may be aligned at one or more designated alignments points with the membrane. For example, alignment posts of the body portions may pass through alignment holes formed in the outer membrane portion. Alternatively, a peripheral edge of at least one of the first and second body portions may be aligned with a peripheral edge of the membrane.

At least an outer portion of the valve seat preferably has a uniform height such that, when the valve is closed, the inner portion of the membrane uniformly seals around the valve seat. In some applications it may be desired that the valve seat has a uniform height across its breadth but since it is the outer portion of the valve seat that contacts the valve membrane first as the valve closes, it is particularly advantageous that at least the outer portion of the valve seat has a uniform height.

To isolate the fluidic region of the valve from non-fluidic regions of the valve, to prevent leakage, at least one of the first and second body portions may have a channel formed therein, and compressible sealing material may be disposed within the channel for sealing the valve as the first and second body portions are brought together.

It will be appreciated by those skilled in the art that various materials may be used as the membrane material, including rubber, silicone and elastomer.

According to a second aspect of the present invention there is provided a pump comprising the valve according to the first aspect of the present invention. The pump may be a pump for pumping liquid therapeutic products, comprising a pumping chamber having an inlet and an outlet, means for causing a change in a volume in the pumping chamber, wherein at least one of the inlet and outlet includes the valve according to the first aspect of the present invention.

To reduce the overall volume of the pump, a portion of the pumping chamber volume may be bounded by the inner membrane portion of the valve. A fluid conduit may connect the pumping chamber to a fluid inlet of the outlet valve.

Preferably, the inlet valve has a lower activation pressure than the outlet valve to prevent uncontrolled flow of therapeutic product through the pump. The difference in activation pressure between the inlet valve and the outlet valve may be effected by providing similar inlet and outlet valves, wherein a height of the valve seat of the outlet valve is greater than a height of the valve seat of the inlet valve. In other words, the valve seat of the inlet valve extends beyond the plane of the outer membrane portion of the inlet valve towards the inner membrane portion to a lesser extent than does the valve seat of the outlet valve.

According to a third embodiment of the present invention, there is provided an infusion system including the pump according to the second aspect of the present invention. The infusion system preferably comprises a reservoir of therapeutic product held at a positive pressure with respect to the ambient pressure. Liquid therapeutic product may be pumped by the pump according to the second aspect of the present invention through a tube to a cannula that pierces a patient's skin. The infusion system may be programmable to supply a desired rate of delivery of the therapeutic product to the patient.

The valve and pump of the present invention are preferably micro components and the pumping chamber of the pump has a volume preferably less than approximately 100 μl.

BRIEF DESCRIPTION OF THE DRAWINGS

Examples of the present invention will now be described in detail with reference to the accompanying drawings, in which.

DETAILED DESCRIPTION

Figure 1:
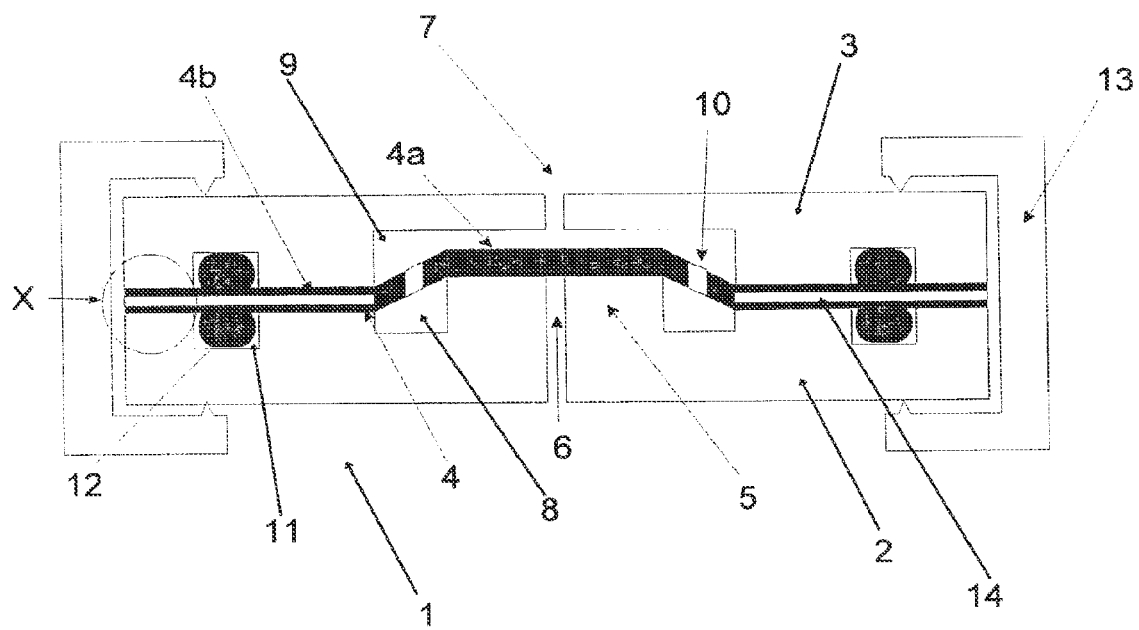
FIG. 1 is a cross-section view of a valve in accordance with a first embodiment of the present invention.

Turning firstly to FIG. 1 there is shown the first embodiment of the valve in accordance with the present invention. The valve 1 comprises a first body portion 2, a second body portion 3 and a membrane 4 trapped between the first and second body portions 2,3. The membrane 4 comprises an inner portion 4a and an outer portion 4b. The valve 1 is essentially rectangular. However, it will be understood that other shapes may be suitable such as cylindrical, hexagonal, octagonal, or square. The first body portion 2 has a raised valve seat 5 that extends beyond a plane of the outer membrane portion 4b such that the inner membrane portion 4a is stretched over the valve seat 5. The inner membrane portion 4a and at least a portion of the outer membrane portion 4b are formed of elastomeric rubber material.

A valve inlet 6 is formed in the valve seat 5 and a valve outlet 7 is disposed opposite the inlet 6 on the other side of the membrane 4 from the inlet 6. Cavities 8 and 9 are formed in the first and second body portions 2,3, respectively adjacent apertures 10 formed through the membrane 4.

Channels 11 are formed in the first and second body portions 2,3 and compressible sealing rings 12 are disposed in the channels 11. The first and second body portions 2,3 trap the outer portion 4b of the membrane 4 when the first and second body portions 2,3 are clamped by clamps 13 and the sealing rings 12 compress to seal the valve 1.

The outer peripheral portion 4b of the membrane 4 includes a substantially rigid frame-like structure 14 encased in the membrane elastomeric rubber material. Contact between two adjacent "hard" surfaces is denoted by point X in FIG. 1. By ensuring that the contact point is reproducible tight control on the amount by which the inner membrane portion 4a is stretched over the valve seat 5 is obtained. As will be explained in further detail in the following the outer peripheral portion 4b may be substantially incompressible such that contact between the first and second body portions 2,3 and the outer peripheral portion 4b of the membrane 4 may be at points where no compression is possible, i.e. the meeting surfaces are "hard". This provides the advantage that the amount by which the valve seat 5 extends beyond the plane of the outer membrane portion 4b is controlled by these contact points and riot by features of the process or equipment by which the valve is manufactured.

In use, fluid enters under a positive pressure into the inlet 6. Above a predetermined fluid pressure, the inner membrane portion 4a becomes unseated from the valve seat 5 as the inner membrane portion 4a deflects under the fluid pressure at the inlet 6. The pressure at which this occurs is known as the activation pressure of the valve. Upon breaking the seal between the inner membrane portion 4a and the valve seat 5, fluid flows from the inlet 6 over a head of the valve seat 5 and into the cavity 8 formed in the first membrane portion 2. Fluid passes through the apertures 10 formed in the membrane 4 into cavity 9 formed in the second body portion 3 which fluidically connects to the outlet 7. Therefore, when the valve is open, fluid passes from the inlet 6 through the apertures 10 and through outlet 7.

As the fluid pressure in the inlet 6 is decreased, due to external forces acting on the fluid, below a predetermined activation pressure, the inner membrane portion 4a re-seals with the valve seat 5 to cut off the fluid path between the inlet 6 and the apertures 10. Fluid can therefore no longer pass from the inlet 6 to the outlet 7 via the apertures 10 and so the valve is closed. Return of an inlet pressure higher than the predetermined activation pressure of the valve 1 once again opens the valve. The activation pressure at which the valve opens may be slightly different to that at which the valve closes due to static and dynamic properties of the fluid.

The rigid frame 14 encased in the membrane elastomeric rubber material in the outer peripheral portion 4b of the membrane 4 serves to make more rigid the outer peripheral membrane portion 4b than the inner membrane portion 4a. The membrane 4 may be formed by moulding the elastomeric rubber material of the membrane around the rigid member 14. The rigid member 14 restricts deformation of the membrane 4 to substantially only the inner portion 4a of the membrane 4. By restricting the portion of the membrane 4 that can deflect, the activation pressure at which the valve 1 opens can be accurately defined. The activation pressure is also dependent on such factors as the height of the valve seat 5 with respect to the plane of the outer membrane portion 4b, the number and arrangement of the apertures 10 and the material composition of the inner membrane portion 4a. The inner membrane portion 4a is accurately positioned with respect to the valve seat 5 as described previously to control the activation pressure.

Since the activation pressure of the valve 1 is dependent on the height of the valve seat 5, a range of valves similar to the valve 1 may be constructed wherein the only variable is the height of the valve seat 5 thereby providing a range of valves having different predetermined activation pressures using mostly common parts and common construction techniques. This dramatically saves on production and design costs and enables inexpensive, disposable valves to be produced in high volumes. The valve 1 may also be manufactured in relatively large batches with accuracy such that a batch of similarly specified valves 1 will operate at virtually identical activation pressures.

To isolate the fluidic regions of the valve 1, namely those forming part of the fluid path from the inlet 6 via the cavities 8, 9 and the apertures 10 to the outlet 7, from non-fluidic regions of the valve, such as the peripheral edges, the sealing rings 12 of compressible elastomeric material are provided in the grooves 11 which compress as the first and second body portions 2,3 are brought together and retained by clamps 13. It will be appreciated by those skilled in the art that instead of clamps 13, other fixing means for fixing the first and second body portions to trap the membrane 4 therebetween such as gluing, welding, or clipping may be provided. The clamping means 13 are shown as a purely exemplary means of how the first and second body portions 2,3 of the valve 1 may be retained.

Due to the way in which the inner membrane portion 4a is stretched over the valve seat 5, and the way in which the fluid flows between the valve seat 5 and the inner membrane portion 4a when the valve is open, it is important that at least an outer portion of the valve seat 5 has a uniform height such that, when the valve is closed, the inner portion 4a of the membrane uniformly seals around the valve seat 5. Since it is the outer portion of the valve seat 5 which seals first as the valve closes and which releases last as the valve opens, it is not so important that the valve seat 5 has a perfectly uniform head. However, this may be desirable in some applications.

In the first embodiment of the present invention, the rigid frame member 14 is provided of metal, glass, ceramic or polymer material. However, it will be appreciated by those skilled in the art that the purpose of the rigid frame member 14 is to stiffen the outer peripheral portion 4b of the membrane 4 with respect to the stiffness of the inner membrane portion 4a. To achieve a similar aim, the outer peripheral portion 4b of the membrane 4 may have a different material composition, or dimension, to that of the inner membrane portion 4a.

The geometry of the valve 1 that is designed to have a predetermined activation pressure may be designed through either theoretical calculation, finite element analysis (FEA) modelling or the like, or experimentation. The dynamic function of the valve may also be modelled in this way such that the amount of deflection of the inner membrane portion 4a and the fluid flow from the valve inlet 6 to the valve outlet 7 may be precisely defined.

Figure 2:
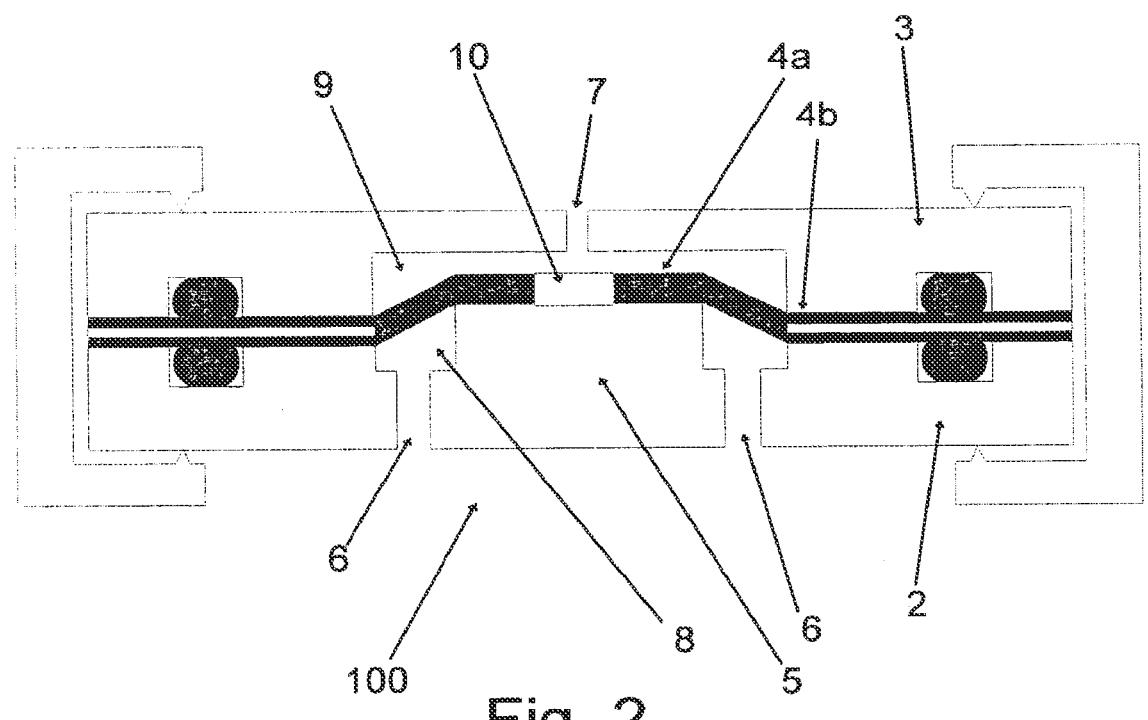
FIG. 2 is a cross-section view of a valve in accordance with a second embodiment of the present invention.

FIG. 2 illustrates a second embodiment of the valve in accordance with the present invention wherein like parts are designated by like reference numerals with those of the first embodiment of the present invention. The difference between the second embodiment when compared with the first embodiment of the present invention is that the valve 100 has two inlets 6 and a single aperture 10 is formed in the membrane portion 4a.

In use, a positive fluid pressure at the valve inlets 6, which may be fluidically connected, open into the recess 8 formed in the first body portion 2. Above a predetermined activation pressure, the fluid pressure in the cavity 8 causes the inner membrane portion 4a to deflect from the valve seat 5 thus creating a fluid path between the valve seat 5 and the inner membrane portion 4a such that fluid may pass through the single aperture 10 formed in the inner membrane portion 4a. Thus, when the valve is open, fluid may pass from the fluid inlets 6, via the cavity 8, the aperture 10 and the cavity 9, to the outlet 7. Upon a decrease in the fluid pressure at the valve inlets 6, the inner membrane portion 4a re-seals with the valve seat 5 thus closing the valve such that fluid may no longer pass from the inlets 6 through the aperture 10 to the outlet 7. Again, it is important that an outer peripheral portion of the valve seat 5 has a uniform height so as to create a uniform seal with the inner membrane portion 4a at the activation pressure. The clamping arrangement of the valve 100 is identical to that as for the valve 1.

It will be appreciated by those skilled in the art that modifications of the valve 1 may be equally applicable to the valve 100.

Figure 3:
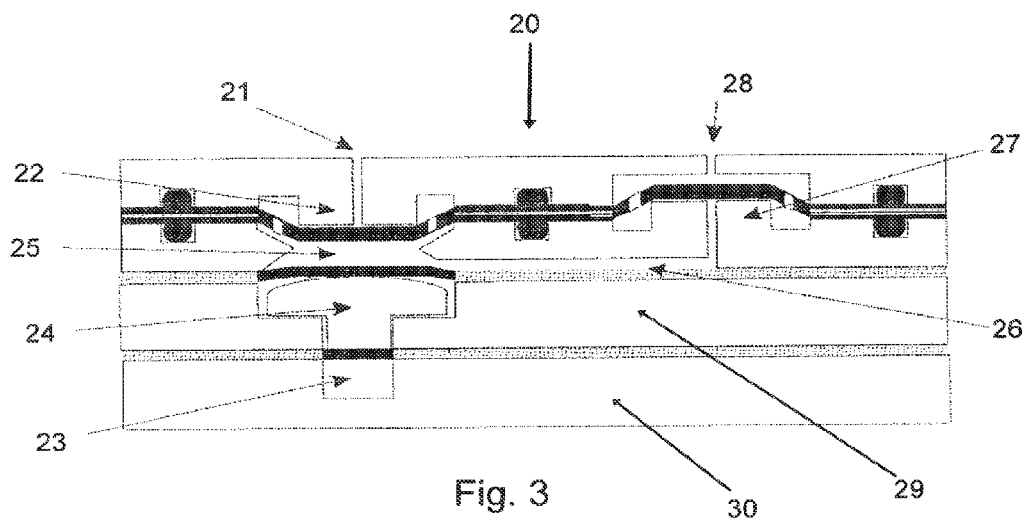
FIG. 3 is a cross-section view of a pump comprising the valves of FIG. 1.
Figure 4:
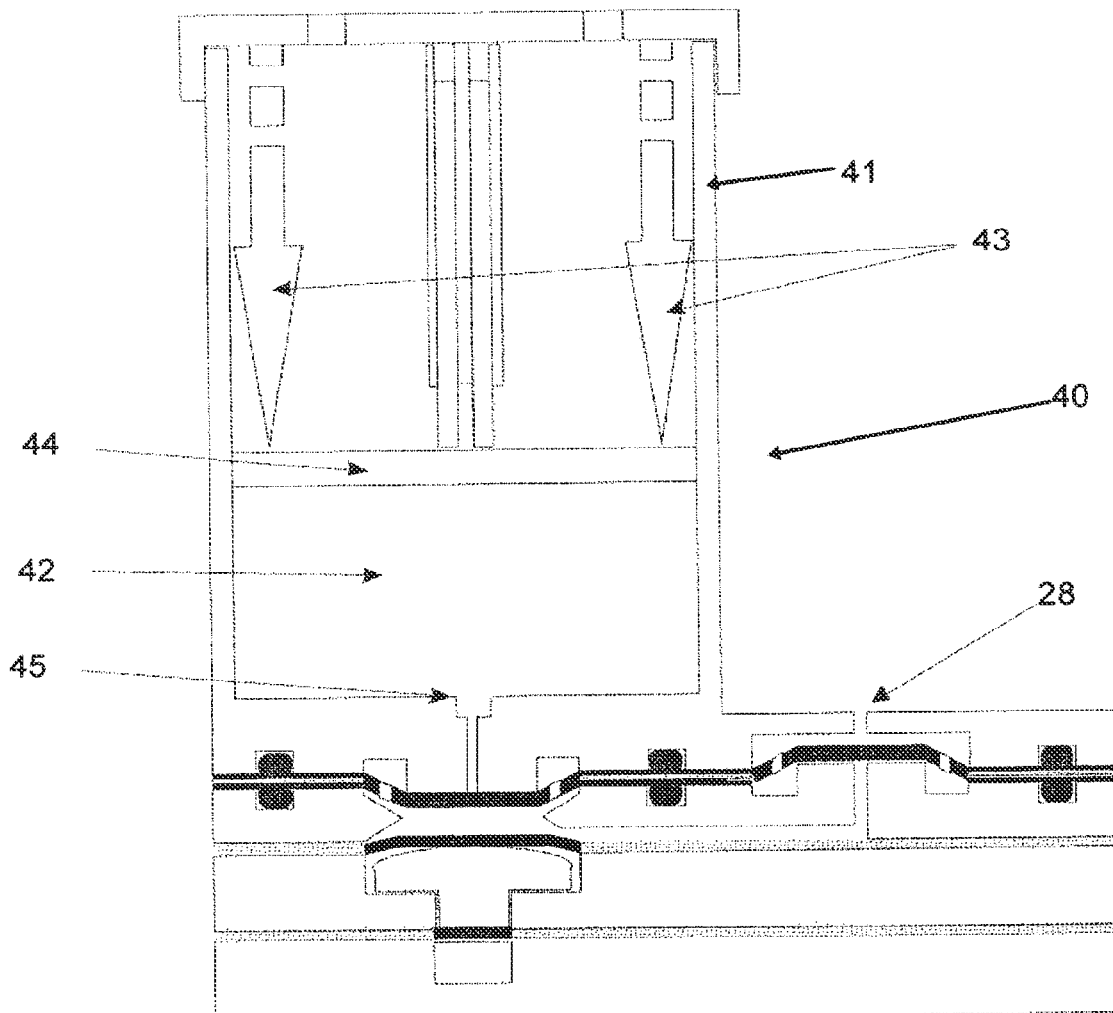
FIG. 4 illustrates the pump of FIG. 3 as part of an infusion system.

An example of an application of the valve 1 in a pump is shown in FIG. 3. The pump 20 has a fluid inlet 21 leading to an inlet valve 22. Operation of an actuator 23 having a gearing assembly 24 causes a change in volume of a pumping chamber 25. An outlet of the inlet valve 22 is fluidically connected by conduit 26 to outlet valve 27.

The outlet valve 27 has a structure substantially identical to the valve 1 of the first embodiment of the present invention. The inlet valve 25 has a slightly different configuration to the valve 1 since a portion of the pumping chamber 25 is bounded by the membrane of the valve 22. Whilst the inlet valve 22 constitutes a part of the pumping chamber 25 in the particular embodiment shown in FIG. 3, it will be appreciated by those skilled in the art that the pumping chamber may be provided between the inlet valve 22 and the outlet valve 27, although this would increase the overall volume of the pump.

The actuator 23 is preferably a wax-type actuator comprising a reservoir of wax sealed by a resiliently deformable diaphragm. Upon heating the wax in the reservoir, the volume of the wax expands to deflect the resiliently deformable diaphragm. Linear deflection of the diaphragm can be harnessed to provide mechanical work. Upon cessation of heating of the wax, the wax in the reservoir cools and the diaphragm sealing the wax reservoir returns to its original position. The wax-type actuator can therefore be used to perform cyclical linear movements.

As an alternative to a wax-type actuator other actuators are known in the art, such as solenoid and piezo-electric actuators, which can produce similar cyclical linear displacements.

To increase the volume deflection of the actuator 23, a gearing assembly 24 is provided. The gearing assembly 24 comprises a gearing piston and a gearing diaphragm which forms a part of the boundary of the pumping chamber 25. The piston is connected, or positioned in contact with, the diaphragm of the actuator 23. Movement of the piston is restrained within walls of a gearing layer 29 of the pump. The actuator 23 is similarly disposed within side walls of an actuator layer 30 to achieve correct alignment of the gearing assembly 24 and the actuator 23. Deflection of the actuator diaphragm causes the piston of the gearing assembly 24 to move thus deflecting the gearing diaphragm. The gearing diaphragm is larger than the actuator diaphragm and so the volume displacement of the gearing diaphra is significantly greater than the volume displacement of the actuator diaphragm.

Since the gearing diaphragm forms a part of the pumping chamber 25, the volume of the pumping chamber 25 can be increased, or decreased, by operation of the actuator 23. Upon increasing the volume of the pumping chamber 25, the inlet valve 22 opens and fluid flows from the inlet 21 through the inlet valve 22 to fill the pumping chamber 25. Once the pumping chamber 25 is full, operation of the geared actuator 23, 24 to reduce the volume of the pumping chamber 25 forces the fluid along conduit 26 to outlet valve 27. Since the fluid passing through the conduit 26 is under pressure from the geared actuator 23,24, the outlet valve 27 opens and fluid exits the pump via outlet 28.

Since the outlet valve 27 closes when the fluid pressure in the conduit 26 decreases below a predetermined value, fluid cannot pass through the outlet valve from the outlet 28 to the fluid conduit 26. Operation of the geared actuator 23,24 to once again increase the volume of the pumping chamber 25 causes the inlet valve 22 to open thus permitting fluid to flow from the inlet 21 to fill the pumping chamber 25. Repeated operation of the geared actuator 23,24 causes fluid to be pumped from the inlet 21 to the outlet 28 of the pump 20.

The height of the valve seat of the outlet valve 27 is higher than the height of the valve seat of the inlet valve 22. Otherwise, the structure of the valves 22 and 27 is substantially identical. Therefore, the activation pressure of the outlet valve 27 is higher than the activation pressure of the inlet valve 22. As will be appreciated by those skilled in the art from the foregoing the activation pressure of the outlet valve 27 may be made higher than the activation pressure of the inlet valve 22 also by altering parameters of the valves such as the dimension, arrangement and material of the membranes and the number of holes in the membranes, for example. The higher activation pressure of the outlet valve 27 ensures that even though a positive fluid pressure may be supplied at inlet 21 of the pump 20, free flow of fluid through the pump 20 from the inlet 21 to the outlet 28, even in the case of a failure of the actuator 23, cannot occur. This is particularly important in the case where the pump 20 is used as part of an infusion system where free flow of liquid therapeutic product through the pump 20 would be unacceptable. The inlet valve 22 has a relatively low activation pressure to ensure that upon operation of the geared actuator 23,24 the pumping chamber 25 fills with liquid from the inlet 21 quickly with minimal delay in opening of the valve 22.

The pump 20 described with reference to FIG. 3 finds particular use in an infusion system for the delivery of therapeutic products into a human or animal body. The infusion system 40 is shown in FIG. 7 and includes a pressurised reservoir 41 of therapeutic product 42. Therapeutic product 42 is pressurised within the reservoir by application of a force, indicated by arrows 43, on a plunger 44 movable within the reservoir cavity. An outlet 45 of the reservoir is connected to the inlet 21 of the pump 20. Means for fluidically coupling the pump 20 to a human or animal body to which the therapeutic product is to be delivered are connected at one end to the patient, and at the other end to the outlet 28 of the pump 20. This means may be a cannula or other similar device.

The actuator 23 is preferably controlled by an electronics module (not shown) that works in cooperation with at least one flow rate indicator to ensure programmed delivery of the therapeutic product with a high degree of accuracy.

It is envisaged that the valve 1 and pump 20 are micro components and the pumping chamber of the pump has a volume preferably less than approximately 100 μl.

Various modifications of the present invention are envisaged as will be appreciated by the skilled person without departing from the scope of the invention, which is defined by the appending claims.

The invention claimed is:

1. A one-way valve comprising:
   a seat; and
   a membrane having an inner portion, and an outer peripheral portion, the inner portion being stretched over the seat, and in use, selectively deflected therefrom such that a fluid path is created from one side of the membrane to the other so as to open the valve, the outer peripheral portion of the membrane being stiffer than the inner portion such that the membrane deflection is substantially restricted to only the inner portion the stiffening of the outer peripheral membrane portion relative to the inner membrane portion being effected by a rigid frame embedded in the outer peripheral portion.

2. A valve according to claim 1, wherein the rigid frame is of a material selected from the group of materials including: metal, glass, ceramic and polymer.

3. A valve according to claim 1, wherein the outer portion of the membrane has a different material composition, or dimension, to that of the inner portion.

4. A valve according to claim 1, wherein the relative stiffness of the inner and outer portions of the membrane is selected according to a desired activation pressure at which the valve opens.

5. A valve according to claim 1, wherein at least one aperture is formed in the membrane that forms a portion of the fluid path across the membrane.

6. A valve according to claim 5, wherein the number and arrangement of the apertures is selected according to a desired activation pressure at which the valve opens.

7. A valve according to claim 1, further comprising a first body portion that includes the valve seat.

8. A valve according to claim 7, wherein the first body portion has a fluid conduit formed therethrough defining an inlet of the valve.

9. A valve according to claim 7, wherein a first cavity is defined by a recess in the first body portion that provides a fluid path from the inlet to the aperture(s) in the membrane when the membrane is displaced from the valve seat as the valve opens.

10. A valve according to claim 7, further comprising a second body portion on the opposite side of the membrane to the first body portion.

11. A valve according to claim 10, wherein the second body portion has a fluid conduit formed therethrough defining an outlet of the valve.

12. A valve according to claim 11, wherein the outlet opens into the second cavity.

13. A valve according to claims 12, wherein the second cavity creates a fluid path between the aperture(s) in the membrane and the outlet.

14. A valve according to claim 10, wherein a second cavity is defined by a recess in the second body portion into which the inner membrane portion moves when the valve opens.

15. A valve according to claim 7, wherein the outer portion of the membrane is fixed to the first body portion.

16. A valve according to claim 15, wherein the fixing of the membrane is by means of clamping, clipping, gluing, bonding or welding.

17. A valve according to claim 10, wherein the outer portion of the membrane is fixed between the first and second body portions.

18. A valve according to any of claims 17, wherein at least one of the first and second body portions is aligned at one or more designated alignments points with the outer membrane portion.

19. A valve according to claim 18, further comprising alignment posts connected to at least one of the first and second body portions that pass through alignment holes formed in the outer membrane portion.

20. A valve according to claim 18, wherein a peripheral edge of at least one of the first and second body portions is aligned with a peripheral edge of the membrane.

21. A valve according to claim 17, wherein at least one of the first and second body portions has a channel formed therein, and compressible sealing material is disposed within the channel for sealing the valve.

22. A valve according to claim 17, wherein at least one of the first and second body portions contact the outer membrane portion at a substantially incompressible interface.

23. A pump according to claim 22, wherein the inlet valve has a lower activation pressure than the outlet valve.

24. A pump according to claim 23, wherein the valve seat of the inlet valve extends beyond a plane of the outer membrane portion of the inlet valve towards the inner membrane portion to a lesser extent than does the valve seat of the outlet valve.

25. A valve according to claim 1, wherein the membrane is of a material selected from the group of materials including: rubber, silicone, and an elastomer.

26. A valve according to claim 1, wherein at least an outer portion of 25 the valve seat has a uniform height such that, when the valve is closed, the inner portion of the membrane uniformly seals around the valve seat.

27. A pump comprising the valve according claim 1.

28. A pump according to claim 27, for pumping liquid therapeutic product, comprising a pumping chamber having an inlet and an outlet, means for causing a change in a volume of the pumping chamber, wherein at least one of the inlet and outlet includes said valve.

29. A pump according to claim 28, wherein a portion of the pumping chamber volume is bounded by the inner membrane portion of said valve.

30. A pump according to claim 28, wherein a fluid conduit connects the pumping chamber to a fluid inlet of the outlet valve.

31. An infusion system including the pump of claim 27.

* * * * *